United States Patent [19]
Cool

[11] Patent Number: 5,864,892
[45] Date of Patent: Feb. 2, 1999

[54] DEVICE AND METHOD FOR COLLECTING AND SANITIZING TOILET SPRAY

[76] Inventor: Carmen M. Cool, 2116 Kingsford Dr., Florissant, Mo. 63031

[21] Appl. No.: 14,262

[22] Filed: Jan. 27, 1998

[51] Int. Cl.[6] .................................................. E03D 9/02
[52] U.S. Cl. ................................ 4/222; 4/242.1; 4/245.1; 4/300.3
[58] Field of Search ..................... 4/222, 300.3, 242.1, 4/245.1, 245.3–245.8

[56] References Cited

U.S. PATENT DOCUMENTS

| | | |
|---|---|---|
| D. 195,397 | 6/1963 | Whitehorn . |
| D. 252,946 | 9/1979 | Johnson . |
| D. 292,019 | 9/1987 | Hall . |
| D. 314,043 | 1/1991 | Beller . |
| D. 323,027 | 1/1992 | Sanders et al. . |
| 1,967,581 | 7/1934 | Macias . |
| 2,167,587 | 7/1939 | Rowe . |
| 2,286,632 | 5/1942 | Manville . |
| 2,608,694 | 9/1952 | McCamy . |
| 2,910,705 | 9/1959 | Coplan . |
| 2,994,887 | 8/1961 | Thornton . |
| 3,102,276 | 9/1963 | Warnberg . |
| 3,118,149 | 1/1964 | Tomasetti . |
| 4,130,906 | 12/1978 | Robertson . |
| 4,213,212 | 7/1980 | Hefty . |
| 4,227,267 | 10/1980 | Robertson . |
| 4,407,024 | 10/1983 | Schneider . |
| 4,586,202 | 5/1986 | Uchida . |
| 4,589,149 | 5/1986 | Bassi . |
| 4,720,880 | 1/1988 | Barreau . |
| 4,760,613 | 8/1988 | Bobak . |
| 4,766,618 | 8/1988 | Boker . |
| 5,067,185 | 11/1991 | Kohler . |
| 5,144,698 | 9/1992 | McKenzie . |
| 5,745,929 | 5/1998 | Sobieralski ............................ 4/245.1 |
| 5,815,851 | 10/1998 | Perry .................................... 4/300.3 |

*Primary Examiner*—Charles E. Phillips
*Attorney, Agent, or Firm*—Kevin L. Klug

[57] ABSTRACT

A device and method for collecting and sanitizing toilet spray that is removably attachable to a toilet lid and toilet bowl of a conventional toilet. The device and method are capable of absorbing and sanitizing any spray and mist exiting the gaps between the toilet lid, toilet seat and toilet bowl. The device is also capable of absorbing any liquid which runs along the outside of the toilet bowl. The device and method for collecting and sanitizing toilet spray is adapted for quick installation and removal from a conventional toilet and designed for ease of use.

5 Claims, 6 Drawing Sheets

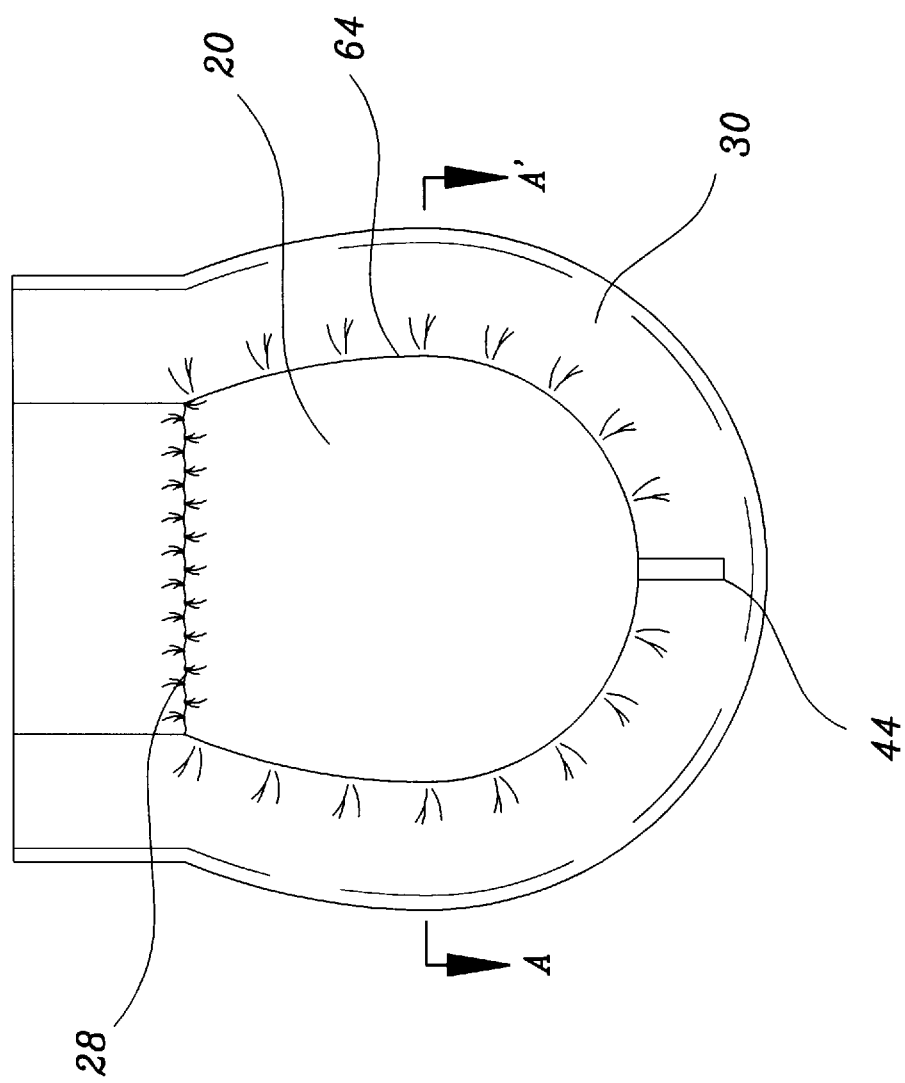

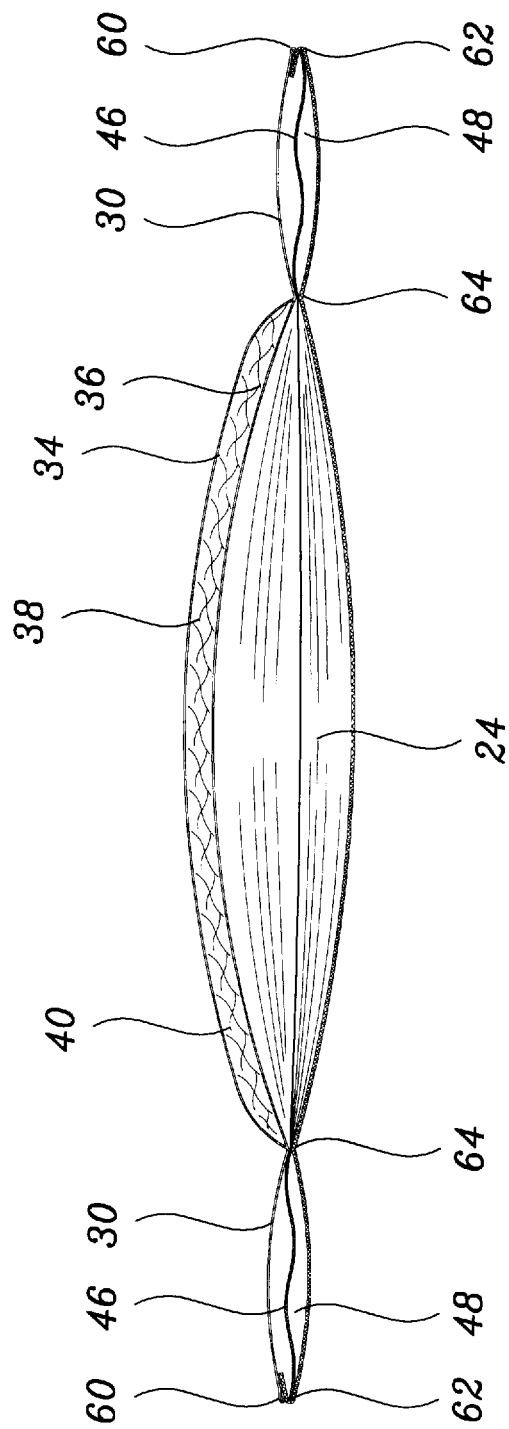

DEVICE AND METHOD FOR COLLECTING AND SANITIZING TOILET SPRAY

BACKGROUND OF THE INVENTION

The present invention relates in general to toilet lid covers and accessories used therewith and pertains, more particularly, to toilet lid cover and drip strip which is used with any conventional toilet and provides an antiseptic protective collector for splashed and sprayed bacterial mist when the toilet is flushed. This invention is an improvement over conventional toilet lid covers and accessories used therewith.

With conventional toilet lid covers no provision is made to ensure that the water splash and mist created during toilet flushing is contained and sanitized within or near the toilet bowl in order to prevent the splash or mist from attaching to persons or things near the bowl. Generally this splash and mist exits the gap between the toilet lid and the toilet seat and/or the gap between the toilet seat and the toilet bowl. Contained within this splash and mist is a rich supply of bacteria from the waste deposited within the toilet. This includes but is not limited to E. coli. As such, it is difficult to maintain a sanitary space near the toilet when using conventional toilet lid covers and accessories therewith.

Accordingly, it is an object of the present invention to provide an improved sanitary toilet lid cover that is adapted for quick installation and removal from a toilet lid and which contains an overhanging curtain and other protection features which cover the gaps where bacterial mist and spray typically exit. The curtain also contains an anti-bacterial cloth which ensures that any bacteria which are collected by the curtain will be killed.

Another object of the present invention is to provide an improved sanitary toilet lid cover which is attached to the toilet lid in such a manner as to not hinder the use of the toilet and a drip strip which fits around the base of the toilet and is used in conjunction with the cover in order to absorb any spray or mist exiting the toilet during flushing thereby providing a sanitary space around the toilet.

A further object of the present invention is to provide an improved sanitary toilet lid cover which contains a handle strap which allows the user to avoid contacting the bacterial collection portion of the cover when raising or closing the toilet lid.

Still another object of the present invention is to provide an improved sanitary toilet lid cover and a drip strip which is able to be used with any conventional toilet.

Still another object of the present invention is to provide a method for containing and sanitizing the spray and mist emitted during the flushing of a toilet with the combination of the sanitary toilet lid cover and the drip strip.

PRIOR ART

Due to the longstanding use of conventional toilets, numerous toilet lid covers have been developed. To date none of the prior art devices or methods have provided a means to collect and sanitize the spray and mist which exits the gaps between the lid and seat and the seat and bowl. Robertson, U.S. Pat. No. 4,130,906 issued Dec. 26, 1978, Coplan, U.S. Pat. No. 2,910,705 issued Nov. 3, 1959 and McCamy, U.S. Pat. No. 2,608,694 issued Sep. 2, 1952 disclose lid covers but provide no method for collection or sanitization of the exiting spray and mist upon flushing of the toilet. Tomasetti, U.S. Pat. No. 3,118,149 issued Jan. 21, 1964 provides a stretchable cover with a lace border for aesthetic reasons but again does not address the exiting spray and mist problem. Warnberg, U.S. Pat. No. 3,102,276 issued Sep. 3, 1963 provides a toilet seat cover which tends to minimize the exiting spray and mist in the gap between the toilet seat and the toilet bowl, but does not prevent spray and mist from exiting between the toilet lid and seat gap nor does it provide any method for sanitization of the spray or mist. Manville, U.S. Pat. No. 2,286,632 issued Jun. 16, 1942 provides a toilet seat cover with a non-absorbing flange which covers a portion of the gap between the toilet bowl and toilet seat. No provision is shown which eliminates the spray and mist exiting between the lid and seat nor is any provision made for absorbing the exiting mist and ensuring the destruction of any bacteria contained within said mist.

SUMMARY OF THE INVENTION

To accomplish the foregoing and other objects of this invention there is provided a device and method for collecting and sanitizing toilet spray which comprises a sanitary toilet lid cover and a drip strip which attach to a toilet lid and the base of a toilet bowl respectively. The sanitary toilet lid cover comprises a pocket formed from an upper semi-oval shaped absorbent material and a lower semi-oval shaped absorbent material which are joined together in such a manner as to form a pocket into which a toilet lid may reside. External to the periphery of the pocket remains enough upper and lower material to provide a curtain which overhangs and covers the gaps between the toilet lid, toilet seat and toilet bowl. Within the curtain, between the upper and lower material, is placed an anti-bacterial cloth which kills bacteria upon contact. This anti-bacterial cloth utilizes technology developed for NASA to help astronauts stay antiseptically clean inside their space suits. It contains a mix of cotton and rayon which is meshed with ultrafine copper and is designed to kill bacteria for up to one year. The periphery of the sanitary toilet lid cover is also joined in order to form a case which secures the anti-bacterial cloth between the upper and lower material and the periphery of the pocket. Around the mouth of the pocket is attached an elastic band which secures the sanitary toilet lid cover to the rearmost portion of the toilet lid.

In a preferred embodiment, the upper semi-oval shaped absorbent material is formed from two layers which form a sandwich containing an absorbent cotton like batting. The upper semi-oval shaped material extends beyond the mouth of the pocket such that the area between the rearmost portion of the toilet lid and the toilet tank may be covered and protected from exiting spray or mist. The cotton like batting serves as an absorbent and as a cushion for persons sitting on the toilet lid. In a preferred embodiment, the lower semi-oval shaped material is formed from an absorbent towel like cotton material.

The drip strip is comprised of a hollow cloth tube which has Velcro® hook and loop fasteners attached to each end. Within the hollow portion an absorbent cotton material or the aforementioned anti-bacterial cloth is placed along with an elastic strip which is attached at both ends near the aforementioned Velcro®. The drip strip is stretched around the base of the toilet bowl and absorbs any liquids or condensation which runs downward and along the external sides of the toilet bowl.

In the preferred embodiment described herein, the combination of the sanitary toilet lid cover and the drip strip ensure that any bacterial liquids exiting the toilet before or during flushing are absorbed before they are able to sit upon any surface or structure beyond the immediate structure of the toilet bowl.

The sanitary toilet lid cover and the drip strip can be manufactured of different materials and in different sizes and colors. In the preferred embodiment described herein they are manufactured from an absorbent cloth material.

BRIEF DESCRIPTION OF THE DRAWINGS

Numerous other objects, features and advantages of the invention should now become apparent upon a reading of the following detailed description taken in conjunction with the accompanying drawings, in which:

FIG. 4 is a top plan view of the preferred embodiment of the sanitary toilet lid cover of the device for collecting and sanitizing toilet spray;

FIG. 5 is a cross-sectional view of the preferred embodiment of the toilet lid cover of the device for collecting and sanitizing toilet spray along line A—A' in FIG. 4 plan view of the toilet lid cover;

DETAILED DESCRIPTION

Figure 1:
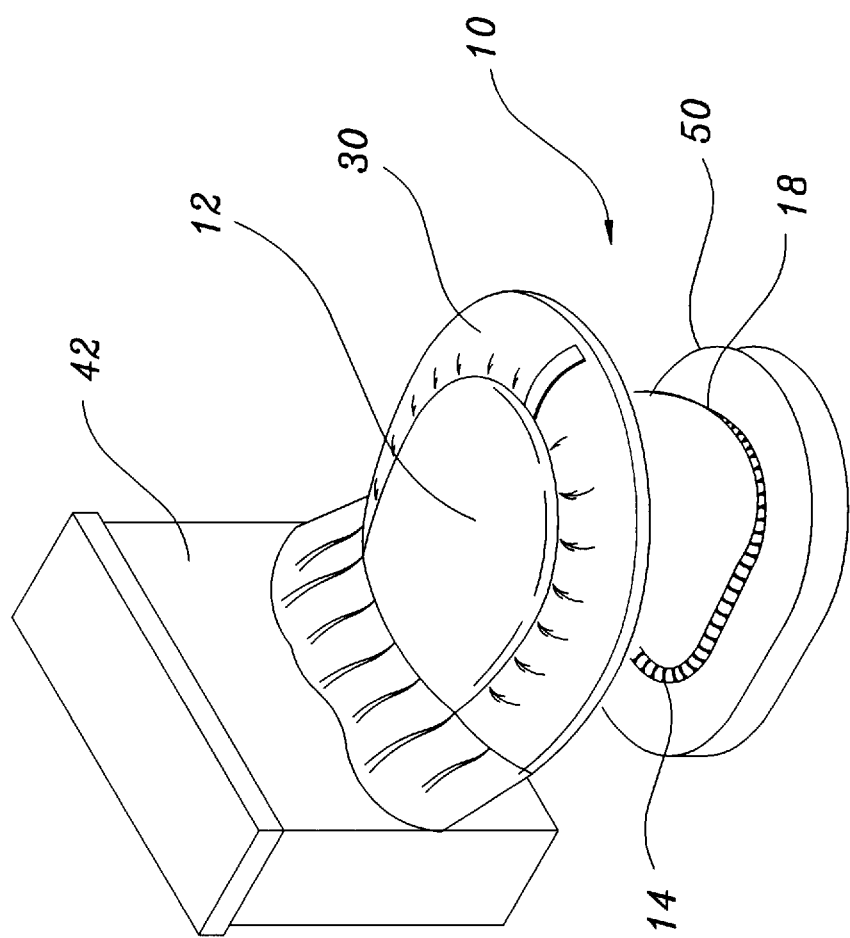
FIG. 1 is a perspective view of a preferred embodiment of the device for collecting and sanitizing toilet spray shown secured onto a toilet.
Figure 2:
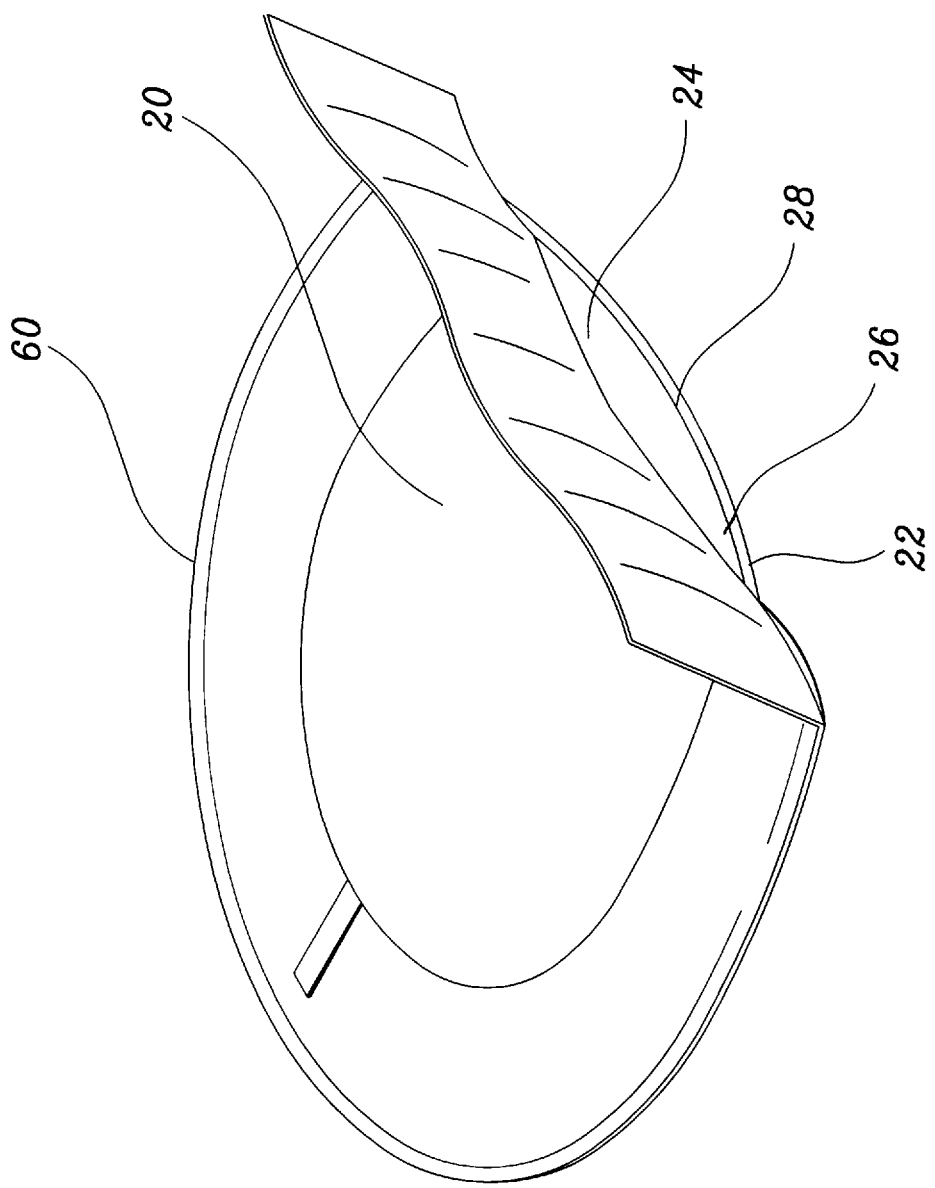
FIG. 2 is a perspective view of the sanitary toilet lid cover of the device for collecting and sanitizing toilet spray not secured to a toilet and showing the mouth portion of the pocket.
Figure 3:
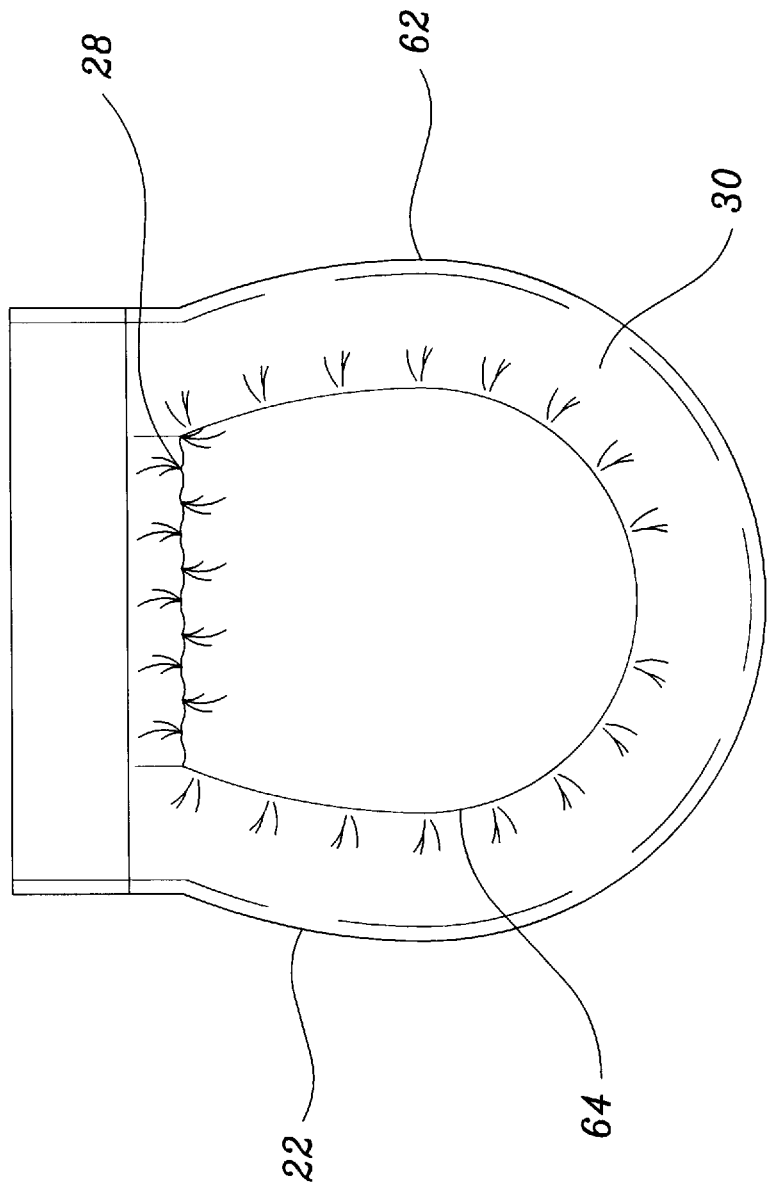
FIG. 3 is a bottom plan view of the preferred embodiment of the sanitary toilet lid cover of the device for collecting and sanitizing toilet spray.
Figure 7:
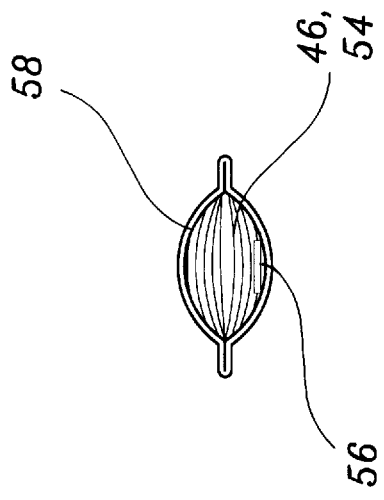
FIG. 7 is a cross-sectional view of the preferred embodiment of the drip strip of the device for collecting and sanitizing toilet spray along line B—B' in FIG. 6 plan view of the drip strip.
Figure 6:
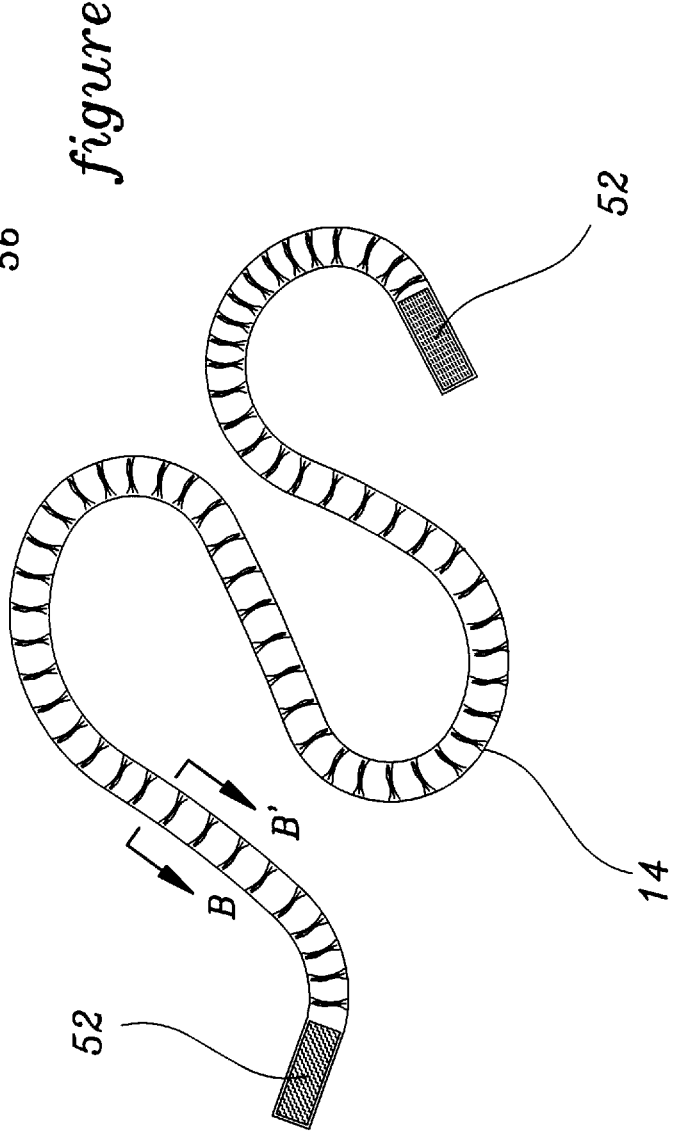
FIG. 6 is a top plan view of the preferred embodiment of the drip strip of the device for collecting and sanitizing toilet spray.

Referring now to the drawings there is shown a preferred embodiment in FIGS. 1–7 of the device for collecting and sanitizing toilet spray of this invention. The device for collecting and sanitizing toilet spray is described in connection with a conventional toilet, including its bowl, seat, lid and tank. The device for collecting and sanitizing toilet spray of the present invention is particularly adapted for attachment to the toilet in such a manner as to not hinder the use of the toilet while also providing for quick installation and removal from the toilet.

The drawings show the device for collecting and sanitizing toilet spray 10 comprising a sanitary toilet lid cover 12 and a drip strip 14 in conjunction with a toilet lid and a toilet bowl 18 respectively.

In a preferred embodiment, the sanitary toilet lid cover 12 comprises an upper semi-oval shaped absorbent material 20, preferably of a fine weave cotton blend cloth, having a first outer edge 60, and a lower semi-oval shaped absorbent material 22, preferably of a cotton towel like material, having a second outer edge 62. The lower and upper material 20,22 are joined, preferably with stitching, to form a pocket 24 into which the toilet lid will fit. Around the mouth 26 of the pocket 24 is sewn an elastic band 28 which provides the necessary tension to secure the sanitary toilet lid cover 12 to the toilet lid. The pocket 24 is of sufficient size to substantially jacket a conventional toilet lid. The upper semi-oval shaped absorbent material 20 extends sufficiently beyond the mouth 26 in order to cover the area between the rearmost portion of the toilet lid and the toilet tank 42 and provide for spray and mist absorption. The periphery 64 of the pocket 24 where the upper and lower material 20,22 is joined to form the pocket 24 is recessed from the outer edges 60,62 of the upper and lower material 20,22 in order to form a curtain 30. The curtain 30 is of sufficient length that it overhangs and covers the gaps between the toilet seat and the toilet lid or toilet bowl 18 when installed on and substantially jacketing the toilet lid, when the toilet lid is in a closed position. Within the curtain 30, between the upper and lower material 20,22 is contained an anti-bacterial cloth 46 which kills any bacteria contained within the spray or mist which is absorbed by the curtain 30. In a preferred embodiment, this anti-bacterial cloth 46 utilizes technology developed for NASA to help astronauts stay antiseptically clean inside their space suits. It contains a mix of cotton and rayon which is meshed with ultrafine copper and is designed to kill bacteria for up to one year. The exact makeup of the material is currently kept as a trade secret by the distributor Real Goods® of Ukiah, Calif. The outer edges 60,62 of the sanitary toilet lid cover 12 are also joined, preferably by sewing, in order to form a case 48, between the upper and lower material 20,22 and the periphery 64 of the pocket 24, into which the anti-bacterial cloth 46 is placed.

The upper semi-oval shaped material 20 is comprised of a first layer 34 and a second layer 36 which form a sandwich 38 containing an absorbent cotton like batting 40. The upper semi-oval shaped material 20 extends beyond the mouth 26 of the pocket such that the area between the rearmost portion of the toilet lid and the toilet tank 42 may be covered and protected from exiting spray or mist. The cotton like batting 40 serves as an absorbent and as a cushion for persons sitting on the toilet lid.

The upper semi-oval shaped material 20 also contains a strip handle 44 on the opposite side from where it is joined to the lower semi-oval shaped material 22 and also opposite the mouth 26 of the pocket 24. The strip handle 44 is used to lift or lower the toilet lid or remove the sanitary toilet lid cover 12 without touching those portions of the sanitary toilet lid cover 12 which may contain bacterial liquids due to flushing.

The drip strip 14 wraps around the base of the toilet bowl 50 and ensures that any liquids emitted during flushing which are not collected by the sanitary toilet lid cover 12 but instead adhere to the exterior of the toilet bowl 18 and run downward toward the base of the toilet bowl 50 are absorbed. The drip strip 14 is comprised of a hollow cloth tube 58 with two ends, preferably of fine cotton mesh, which has Velcro® hook and loop fasteners 52 attached to each end. Within the hollow portion, preferably an absorbent material 54 or the aforementioned anti-bacterial cloth 46 is placed along with an elastic strip 56 which is attached at both ends near the aforementioned Velcro® 52. The elastic strip 56 allows the drip strip 14 to stretch and secure itself around the base of the toilet bowl 50.

The method of installation of the device for collecting and sanitizing toilet spray 10 is quick and easy. The user simply stretches the elastic band 28 at the mouth 26 of the pocket 24 of the sanitary toilet lid cover 12 enough to fit the upper and lower material 20,22 over the toilet lid and place the toilet lid substantially within the pocket 24. The user then releases the elastic band 28 near the rear of the toilet lid in order to secure the sanitary toilet lid cover 12 to the toilet lid. When secure, the curtain 30 will hang downward to cover the gaps between the toilet seat and the toilet bowl 18 and/or the toilet lid. The user then stretches the drip strip 14 around the base of the toilet bowl 50 and secures it in place by joining the Velcro® 52 strips together.

Operation and method of use of the device for collecting and sanitizing toilet spray 10 simply requires the user to lift the toilet seat by pulling upward on the strip handle 44 before using the toilet. After toilet use, the user simply lowers the toilet lid by closing it with the strip handle 44, while ensuring that the curtain 30 covers any gaps between the toilet lid, seat and bowl 18, and flushes. Any mist, spray or liquid which is emitted, is collected by the curtain 30 and sanitized or drips along the exterior of the toilet bowl 18 and is absorbed by the drip strip 14. If the drip strip 14 contains the anti-bacterial cloth 46 then any liquid absorbed by it is also sanitized.

From the foregoing description those skilled in the art will appreciate that all objects of the present invention are realized. A device for collecting and sanitizing toilet spray 10 and a method of use has been shown and described which permits attachment to a toilet in such a manner as to not hinder the use of the toilet while also providing for quick installation and removal.

Having described the invention in detail, those skilled in the art will appreciate that modifications may be made of the invention without departing from its spirit. Therefore, it is not intended that the scope of the invention be limited to the specific embodiments illustrated and described. Rather it is intended that the scope of this invention be determined by the appended claims and their equivalents.

What is claimed is:

1. A device for collecting and sanitizing toilet spray emitted during flushing of a conventional toilet having a toilet lid, a toilet seat, a toilet tank and a toilet bowl comprising:

a sanitary toilet lid cover formed by joining an upper semi-oval shaped absorbent material having a first outer edge and a lower semi-oval shaped absorbent material having a second outer edge, to form a pocket;

said pocket having a mouth and a periphery and capable of substantially jacketing said toilet lid, said periphery recessed from said first outer edge and said second outer edge; and said upper semi-oval shaped absorbent material extending sufficiently beyond said mouth to cover an area between said toilet lid and said toilet tank when said pocket is jacketing said toilet lid; and an elastic band sewn into said mouth of said pocket; and said first outer edge and said second outer edge also joined, except at said mouth of said pocket, to form a curtain, between said outer edges and said periphery of said pocket, and a case between said upper semi-oval shaped absorbent material, said lower semi-oval shaped absorbent material, said outer edges and said periphery of said pocket;

said curtain having sufficient length between said outer edges and said periphery of said pocket to hang over and cover gaps existing between said toilet lid and said toilet seat and said toilet seat and said toilet bowl when said toilet lid is in a closed position; and an anti-bacterial cloth placed within said case whereby bacteria contained in moisture absorbed by said curtain are killed.

2. The device for collecting and sanitizing toilet spray emitted during flushing of a conventional toilet as set forth in claim 1 said device further comprising:

a drip strip having two ends and formed from a hollow cloth tube of sufficient length to wrap around the base of said toilet bowl; and said drip strip having hook and loop fasteners attached to each of said two ends whereby said ends may be joined after wrapping around the base of said toilet bowl; and said drip strip having an absorbent material and an elastic strip placed within said hollow cloth tube, said elastic strip attached at each of said ends whereby said drip strip may be stretched and secured around the base of said toilet bowl.

3. The device for collecting and sanitizing toilet spray emitted during flushing of a conventional toilet as set forth in claim 2 said device further comprising:

a strip handle attached to said upper semi-oval shaped absorbent material whereby said sanitary toilet lid cover may be lifted or removed.

4. The device for collecting and sanitizing toilet spray emitted during flushing of a conventional toilet as set forth in claim 3 said upper semi-oval shaped absorbent material further comprising:

a first layer and a second layer joined together to form a sandwich; and an absorbent cotton like batting placed within said sandwich.

5. The device for collecting and sanitizing toilet spray emitted during flushing of a conventional toilet as set forth in claim 2 said absorbent material comprising:

a strip of said anti-bacterial cloth.

* * * * *